United States Patent [19]

Cordon

[11] 4,060,599
[45] *Nov. 29, 1977

[54] DENTIFRICES

[75] Inventor: Martin Cordon, Highland Park, N.J.

[73] Assignee: Colgate-Palmolive Company, New York, N.Y.

[*] Notice: The portion of the term of this patent subsequent to May 18, 1993, has been disclaimed.

[21] Appl. No.: 675,098

[22] Filed: Apr. 9, 1976

Related U.S. Application Data

[63] Continuation-in-part of Ser. No. 561,842, March 25, 1975, Pat. No. 3,957,968, which is a continuation-in-part of Ser. No. 389,826, Aug. 20, 1973, abandoned, which is a continuation-in-part of Ser. No. 355,365, April 30, 1973, abandoned.

[51] Int. Cl.$^2$ .......................... A61K 7/16; A61K 7/26
[52] U.S. Cl. ...................................................... 424/49
[58] Field of Search ....................... 424/57, 49, 52, 54, 424/58

[56] References Cited

U.S. PATENT DOCUMENTS

| | | | |
|---|---|---|---|
| 3,003,919 | 6/1956 | Broge | 424/49 |
| 3,060,098 | 10/1962 | Gershon | 424/57 |
| 3,325,368 | 6/1967 | Wood et al. | 424/52 |
| 3,670,076 | 6/1972 | Muhler | 424/49 |
| 3,906,090 | 9/1975 | Colodney | 424/52 |

Primary Examiner—Henry R. Jiles
Assistant Examiner—Cary Owens
Attorney, Agent, or Firm—Robert L. Stone; Murray M. Grill; Herbert S. Sylvester

[57] ABSTRACT

Dentifrices containing ground crystals of alpha-alumina having a mean ultimate particle size of about 1 to 2 microns. Typically, the size is that essentially 100% are below 10 microns; about 95% are below 5 microns; about 85% are below 3 microns; about 75% are below 2 microns; about 25% are below 1 micron; and about 5% are below 0.5 microns.

6 Claims, No Drawings

DENTIFRICES

This application is a continuation-in-part of my copending application Ser. No. 561,842, filed Mar. 25, 1975, now U.S. Pat. No. 3,957,968, issued May 18, 1976, which is a continuation-in-part of Ser. No. 389,826, filed Aug. 20, 1973, and now abandoned, which is a continuation-in-part of application Ser. No. 355,365 filed Apr. 30, 1973, and now abandoned.

This invention relates to dentifrices.

One aspect of this invention relates to a dentifrice having outstanding cleaning and polishing characteristics and containing a dental abrasive having a particle size of about 1 to 2 microns and a Mohs hardness of less than about 6 (e.g., 2 to 5) and ground crystals of alpha-alumina, ground to its ultimate crystalline form and having a mean ultimate crystalline particle size of about 1 to 2 microns.

the alpha-alumina crystals are a low-soda ceramic alumina material typically commercially available from Reynolds Chemicals Company, Richmond, Virginia, as RC-152 DBM. This material is described in the brochure Reynolds Calcined Alumina RC-152 issued by Reynolds Chemical Compay under the designation "Adv. No. 733-1-8 (3-870)", the disclosure of which is incorporated herein by reference.

These crystals when ground by conventional means to obtain ultimate particles, such means typically being by dry grinding an alumina sample (e.g. 125 grams) in a ball mill (e.g., a 1.83 gallon ball mill) with high alumina balls (e.g., 4000 grams, 1 inch diameter balls) for several (e.g., about 4) hours. Typically the speed of the mill is about 62 – 64 rpm.

The product obtained, available commercially as RC-152 DBM is very dense and highly stable. It has a mean particle size between about 1 to 2 microns, typically about 1.6 microns. Its typical size distribution is as follows:

| Particle Diameter | Percent of Particles Finer than corresponding diameter |
|---|---|
| 10 | about 100 |
| 5 | about 95 |
| 3 | about 85 |
| 2 | about 75 |
| 1 | about 25 |
| 0.5 | about 5 |

Under an electron miroscope the larger particles appear flat with sharp sides and the smaller irregularly rounded in circular and oval shapes.

Crystalline alumina RC-152 DMB is ground from a coarser alumina commercially available as RC-152. RC-152 has a crystal particle size such that 98% of the particles pass through a 325 mesh (U.S. Standard Sieve) screen, 90% pass through a 200 mesh screen and 25% pass through a 100 mesh screen.

The crystalline alpha alumina has been observed to be chemically.

| | % by weight | ppm |
|---|---|---|
| $Al_2O_3$ | 99.7 | |
| $Na_2O$ | 0.04 | |
| $SiO_2$ | 0.065 | |
| $Fe_2O_3$ | 0.024 | |
| $TiO_2$ | 0.0016 | |
| $MnO$ | 0.0012 | |
| $CaO$ | 0.045 | |
| $Cr_2O_3$ | 0.00036 | |
| $B_2O_3$ | 0.001 | |
| $F_2$ | | 200 |
| alpha phase alumina | < 90 | |

The grade RC-152 DBM has a green compaction density, determined on 20 gram pellets pressed at 4000 psi in a 1 inch diameter steel die, of 2.27 g/cc and a fired density determined after firing green pellets for 1 hour at 1620° C, of 3.75 g/cc. Its linear shrinkage, determined as the average of the fired pellets measured for diameter and height shrinkage between the green pressed pellet and the fired pellet is 15.5%.

The presence of the described crystalline alpha-alumina particles is found to impart improved tooth polishing and tooth cleaning and stain removal characteristics to the dentifrice in comparison to such characteristics obtained with grades of alpha-alumina which when ground to ultimate crystals are larger or smaller. Also they are desirable in highly flavored toothpastes.

The proportion of the ultimate crystal alumina particles in the dentifrice may be for instance, above 0.1% and less than 60%, by weight, e.g., in the range of about 0.2 to 30%, preferably about 1 to 15%, most preferably about 5 – 10%.

The dental abrasive of Mohs hardness less than about 6 may, for instance, be any of these conventionally employed in toothpastes, such as hydrated alumina, anhydrous dicalcium phosphate, calcium pyrophosphate, insoluble sodium metaphosphate, dicalcium phosphate dihydrate, calcium carbonate, silica xerogels of the known high density or intermediate density types (such as those sold under the name Syloid 63 or Syloid 72 of Syloid 74), alkali metal or alkaline earth metal aluminosilicates (such as those having a refractive index of about 1.44 – 1.47, and containing at least about 70% silica, up to about 10% alumina, up to about 20% by weight of moisture and up to about 10% by weight of sodium oxide, the moisture content preferably being about 10 – 20% by weight, measured by loss at 1000° C and the typical content of sodium oxide being about 5 – 10% by weight), kappa-alumina (such as described in U.S. Pat. No. 3,003,919); synthetic resins (such as described in British Pat. No. 995,351); composite abrasive particles in which a hard mineral is coated with, or embedded in, a synthetic resin (the mineral being, for instance, crystalline silica, e.g., quartz, SiC, anhydrous alumina, hematite, ziconium siliate, etc. and the coating being, for instance, an impervious cross-linked thermoset synthetic resin such as melamine-formaldehyde resin, urea-formaldehyde, phenol-formaldehyde, or epoxy resins or polymers or copolymers of compounds having two or more polymerizable ethylenically unsaturated groups, e.g., diallyl phthalate polymers, such as described in U.S. Pat. No. 3,151,027).

The dental abrasive of Mohs hardness less than 6 and particle size about 2 to 40 microns may also be present in the form of relatively large agglomerates (of the individual particles) of such size as to be visible to the naked eye but easily reduced to the fine impalpable particle size upon being subjected to toothbrushing in the mouth. Such agglomerates are described in U.S. Pat. No. 3,574,823, for example; they may be agglomerated with or without binding agent which may be water-soluble or water insoluble.

For most purposes it is preferable that the dental abrasive of Mohs hardness less than 6 have a particle size less than 20 mirons to avoid any gritty feel.

The proportion of such dental abrasive in the dentifrice is usually in the range of about 10 to 60% and is preferably such that when the alpha alumina is omitted from the dentifrice, the dentin abrasion (RDA) is in the range of about 100 to 600, preferably about 100 or 200 to 450. Typically this proportion of dental abrasive is in the range of about 5–70% of the dentifrice, such as about 10–50%.

It is also within the broader scope of this invention to employ the ultimate crystal alpha alumina particles as the sole abrasive in the dentifrice, e.g., in concentrations of about 5 or 10 to 20%. In this case it is often desirable to include other solid ingredients, such as the finely divided thermoplastic polymers mentioned below, so as to provide a toothpaste of suitable consistency.

To make toothpastes or dental creams, the flat flakes of alpha-alumina and the other dental abrasives are dispersed in a dental vehicle which preferably contains a liquid which is water and/or a humectant such as glycerine, sorbitol, propylene glycol or polyethylene glycol 400, including suitable mixture thereof. It is usually advantageous to use a mixture of both water and one or two humectants. Polyethylene glycols of higher molecular weight, e.g., polyethylene glycol 600 etc., may also be present. The total liquid content is generally well over 20% by weight of the vehicle (sorbitol, generally present in admixture with water, is considered as a liquid for this purpose). The preferred humectant are glycerine and sorbitol. Typically the vehicle contains about 0–80% by weight of glycerine, up to about 80% by weight of sorbitol and about 5–80% of water.

The vehicle usually also contains a thickening or gelling agent, such as the natural and synthetic gums and gum-like materials, such as Irish Moss, gum tragacanth, alkali metal (e.g., Li, K or Na) carboxymethyl cellulose and hydroxymethyl carboxyethyl cellulose, polyvinyl pyrrolidone, starch, water soluble hydrophilic colloidal carboxyvinyl polymers such as those sold under the trademark Carbopol 934 and 940, hydroxyethyl cellulose CP or SP, which are each synthetic inorganic complex silicate clays sold under trademark by Laporte Industries, Ltd., and pectin or inorganic thickeners such as colloidal silica, e.g. synthetic finely divided silicas including those sold under the trademarks Cab-O-Sil M5, Syloid 244, Syliod 266 and Aerosil D200. The solid portion of the vehicle is typically present in an amount up to about 10% by weight of the toothpaste and preferably within the range of about 0.5–8% by weight.

Fine particles of thermoplastic resin may also be present, such as particles of solid polymer having a molecular weight above 1000 (and preferably above 10,000, e.g. about 10,000 to 100,000 or more) and a mean diameter less than about 50 microns (preferably in the range of about 0.5 to 50 microns, e.g., about 10 to 30 microns). The polymer particles may be prepared directly by emulsion or suspension polymerizing or by grinding the polymer in bulk, and may be present in amount of up to about 60% or more of the dentifrice, e.g. in the range of about 20 to 60%, such as about 20 to 50%, e.g. about 30 to 50% in a toothpaste. Examples of thermoplastic resins are polymerized ethylenically unsaturated compounds, such as polydefines (e.g. polyethylene or polypropylene) or vinyl or vinylidene resins, such as polyvinyl chloride, polystyrene, vinyl chloride-vinyl acetate copolymers, styrene-butadiene copolymers, polyvinylidene chloride; polyamides such as nylon (e.g. nylon 6); cellulosics such as cellulose acetate, etc.

The toothpaste may also contain surface active agent, e.g. to achieve increased prophylactic action, assist in achieving thorough and complete dispersion of the instant compositions throughout the oral cavity, and render the instant compositions more cosmetically acceptable. The organic surface active material may be anionic, nonionic, ampholytic, or cationic in nature, and it is preferred to employ as the surface active agent a detersive material all which imparts to the composition detersive and foaming properties. Suitable types of such detergents are water soluble salts of higher fatty acid monoglyceride monosulfates, such as sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfonacetates, higher fatty acid ester of 1, 2 hydroxy propane sulfonates, and the substantially saturated higher aliphatic acyl amides of lower aliphatic amino carbyoxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl or N-palmitoyl sarcosine, which should be substantially free from soap or similar higher fatty acid material which tends to substantially reduce the effect of those compounds. The use of these sarcosine compounds in dentifrice compositions of the present invention is particularly advantageous since these materials exhibit a prolonged and marked effect in the inhibition of acid formation in the oral cavity due to carbohydrates breakdown in addition to exerting some reduction in the solubility of tooth enamel in acid solutions.

Other particularly suitable surface active materials include nonionic agents such as condensates of sorbitan monostearate with approximately 60 moles of ethylene oxide, condensates of ethylene oxide with propylene oxide condensates of propylene glycol ("Pluronics") and amphoteric agents such as quaternized imidazole derivatives, which are available under the trademark "Miranol" such as Miranol $C_2M$. Cationic surface active germicides and antibacterial cmpounds such as di-isobutylphenoxyethoxyethyl dimethyl benzyl ammonium chloride, benzyl dimethyl stearyl ammonium chloride, tertiary amines, having one fatty alkyl group (of from 12 to 18 carbon atoms) and two (poly) oxyethylene groups attached to the nitrogen (typically containing a total of from about 2 to 50 ethenoxy groups per molecule) and salts thereof with acids, and compounds of the structure

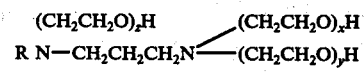

where R is a fatty alkyl group containing from about 12 to 18 carbon atoms, and $x$, $y$ and $z$ total 3 or higher, as well as salts thereof with mineral organic acids, may also be used. It is preferred that the total amount of surface-active agent be a about 0.05 – 5% by weight, preferably about 1 – 3%, of the dentifrice.

Various other materials may be incorporated in the oral preparation of this invention. Examples thereof are coloring or whitening agents, preservatives, silicones, chlorophyll compounds, ammoniated materials, such as urea, diammoniumphosphate and mixtures thereof, and other constituents. Each of these adjuvants may be typically incorporated in the instant toothpastes in amounts up to about 5%.

The toothpaste may also contain antibacterial agents in amounts of about 0.1 –5%. Typical examples of such agents are guanidines, biguanides and amines such as:

N0-(4-chlorobenzyl)-N5-2,4-(dichlorobenzyl) biguanide;
p-chlorophenyl biguanide;
4-chorobenzhydryl biguanide;
4-chlorobenzhydrylguanylurea;
N1-3-lauroxypropyl-N5-p-chlorobenzylbiguanide;
1,6-di-p-chlorophenylbiguanidohexane;
1-(lauryldimethylammonium)-8-(p-chlorobenzyldimethylammonium) oxtane dichloride;
5,6-dichloro-2-guanidinobenzimidazole;
N1-p-chlorophenyl-N5-laurylbiguanide;
5-amino-1, 3-bis (2-ethylhexyl)-5-methylhexahydropyrimidine; and their non-toxic acid addition salts.

Suitable flavoring or sweetening sialagogues may be employed in formulating a flavor for the compositions of the present invention. Examples of suitable flavoring constituents include the flavoring oils, e.g. oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, sorbitol, sodium cyclamate and saccharin. Suitably, flavor and sweetening agents may together comprise from about 0.01 to 5% or more of the compositions of the instant invention.

The compositions of the present invention suitably may also contain a fluorine-containing compound having a beneficial effect on the care and hygiene of the oral cavity, e.g. diminution of enamel solubility in acid and protection of the teeth against decay. Examples thereof include sodium fluoride, stannous fluoride, potassium fluoride, potassium stannous fluoride (SnF$_2$.KF), sodium hexafluorostannate, stannous chlorofluoride, sodium fluorozirconate and sodium monofluorophosphate. These materials, which dissociate or release fluorine-containing ions in water, suitably may be present in an effective but non-toxic amount, usually within the range of about 0.01 to 1% by weight of the water soluble fluorine content thereof.

The dentifrice may be prepared by suitably mixing the ingredients. For instance in making a toothpaste, a gelling agent such as sodium carboxymethyl cellulose or Carbopol 934 and a preservative such as sodium benzoate, if employed, is dispersed with a humectant such as glycerine. Water may also be present. Additional humectant and water, as an aqueous 70% sorbitol solution, may then be mixed with the dispersion and a paste, gel or cream is formed. Dental abrasive agent, surface-active agent and flavor are then added. The toothpaste is then thorougly deaerated (e.g., is vacuo) and tubed.

Preferably the amount of water-soluble essential flavoring oil is above 0.5% and below 2%. Strongly flavored toothpastes contain above about 1% of such flavoring oil, e.g., about 1.2 to 1.5%.

The following Example is given to illustrate this invention further. In this application all proportions are by weight unless otherwise indicated.

EXAMPLE

A toothpaste is prepared containing 24% of the sodium aluminosilicate particles having the following empirical characteristics: silica about 78%; alumina about 1%; sodium oxide about 10%; water (determined by loss on ignition at 1000° C) about 10%; and 10% of the alpha-alumina available from Reynolds Metals Company as RC-152 DBM, together with 25% sodium benzoate; 0.2% sodium saccharine; 0.4% TiO$_2$; 1.5% sodium lauryl sulfate. Flavor and water are also present.

This toothpaste provides about 56% stain removal and a dentin abrasion level (RDA) of about 328, and is quite desirable for these purposes. The enamel abrasion (REA) level is also satisfactory. When other grades of crystals of alpha alumina which when ground to ultimate size are larger and smaller, less desirable results are obtained. For instance, when alpha alumina RC-152 DBM of Reynolds Metals Company, which is ultimately ground to crystals of a mean particle size of about 2.8 microns, is used, the dentin and enamel abrasions are unduly high. Also, when alpha alumina RC-172 DBM of Reynolds Metals Company, which is ultimately ground to crystals of a mean particle size of below 1 micron, is used, poor stain removal is attained.

In a stain removal test, sections of human dental enamel are etched with 0.1N HCl for 2 minutes, rinsed with water, then wet with a dilute solution of stannous fluoride, wiped dry, and finally exposed to a stream of hydrogen sulfide gas which results in the deposition of a brown deposit of stannous sulfide. The amount of stain on the surface is measured with a Gardner Automatic Color Difference meter. The surface is then brushed with a mechanical burshing machine for 500 reciprocal strokes with a slurry of a dentifrice and the residual stain measured with the meter. Finally, the stain which remains is completely removed with dental pumice and the reflectance of this surface is read. The ability of a dentifrice to remove the stain is expressed by the following equation:

(Equation 1)
$$\text{Percent Stain removed} = \frac{(Rd_{500 \, strokes} - Rd_{initial}) \, 100}{Rd_{pumiced} - Rd_{initial}}$$

where $Rd_{initial}$, $Rd_{500 \, strokes}$ and $Rd_{pumiced}$ are respectively the reflectance values measured on the initially stained surface, after brushing 500 reciprocal strokes and after removing the residual stain by pumicing.

The RDA and REA values are obtained by a procedure based on a technique described in the literature; Stookey, C. K. and Muhler, J. C., J. Dental Research 47 524–538 (1968).

It is also within the broader scope of the invention to include other alpha-aluminas, or other abrasives of Mohs hardness above 6, in admixture with the ultimately ground alpha-alumina crystals. For instance, in the Example, one may replace about one-tenth or one-half of the alumina crystals by flat flakes of alpha-alumina having a mean average diameter of less than about 20 microns, typically about 2 to 7 and a thickness of less than about 3 microns; thus, the toothpaste may contain, say, 9% or 5% of the ultimate crystals and 1% or 5% of the flat flakes.

While the ground alpha-alumina crystals have proven most useful thus far in toothpastes, they may also be similarly incorporated into tooth powders or into dental creams which are of pourable consistency.

The pH of the dentifrices is generally within the range of about 4 to 10, e.g., about 5 to 8.

Reference is made herein to copending Application Ser. No. 355,372 of Colodney and Cordon entitle "Dental Polishing Creams", filed on May 3, 1973, whose entire disclosure is incorporated herein by reference.

The particle diameters given in the Example are determined by conventional methods. Thus the standard liquid sedimentation technique may be used, the calculation of particle diameter from the sedimentation data being made (as is conventional) on the basis of Stokes' Law, disregarding the particular shape of the particles.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

I claim:

1. A dentifrice comprising, as an abrasive, ground crystals of alpha-alumina, ground to its ultimate particle form and having a mean ultimate particle size of about 1 to 2 microns, the proportion of said alpha-alumina being above 0.1% and less than 60%.

2. A dentifrice as in claim 1 in which said mean ultimate particle size is about 1.6 microns.

3. A dentifrice as in claim 2 also containing a dental abrasive having a particle size of about 2 to 40 microns and a Mohs hardness of less than about 6.

4. A dentifrice as in claim 3 in which said Mohs hardness is about 2 to 5 and the proportion of said dental abrasive of said Mohs hardness is in the range of about 10 to 60%, the proportion of said alpha-alumina being about 50 to 15%.

5. A dentifrice as in claim 4 containing a sodium alumino-silicate in amount in the range of about 10 to 60%, the proportion of said alpha-alumina being about 5 to 15%.

6. A dentifrice as in claim 5 wherein the proportion of said alpha-alumina is about 10%.

* * * * *